United States Patent [19]

McRobbie

[11] 4,124,628

[45] Nov. 7, 1978

[54] SERIAL ADIABATIC METHANATION AND STEAM REFORMING

[75] Inventor: Henry W. McRobbie, Ossining, N.Y.

[73] Assignee: Union Carbide Corporation, New York, N.Y.

[21] Appl. No.: 819,996

[22] Filed: Jul. 28, 1977

[51] Int. Cl.² .............................. C10J 1/00; C07C 9/04
[52] U.S. Cl. .............................. 260/449 M; 48/197 R; 48/202; 260/449.6 M; 260/449 S
[58] Field of Search ...................... 48/197 R, 202, 206, 48/215; 260/449 M, 449.6 M, 449 S

[56] References Cited

U.S. PATENT DOCUMENTS

| 3,938,968 | 2/1976 | White et al. | 48/197 R |
| 3,958,957 | 5/1976 | Koh et al. | 48/197 R |
| 4,005,996 | 2/1977 | Hausberger et al. | 48/197 R |
| 4,064,156 | 12/1977 | McRobbie | 48/197 R |

OTHER PUBLICATIONS

Woodward, "Catalyst available for high-temperature methanation", Hydrocarbon Processing, Jan.1977, pp 136-138.

Primary Examiner—S. Leon Bashore
Assistant Examiner—George C. Yeung
Attorney, Agent, or Firm—Alvin H. Fritschler

[57] ABSTRACT

A process for the production of methane from a reactant gas comprising $H_2$ and CO employing at least two primary, fixed bed, adiabatic, catalytic reactors in serial arrangement wherein a first feed stream comprised of steam and said reactant gas is reacted in the first of said reactors from a temperature of about 550° F to about 1200° F and wherein a second feed stream comprised of said reactant gas and the effluent gas from said first reactor is reacted in each primary reactor subsequent to the first one from a temperature of about 900° F up to a maximum of about 1600° F.

14 Claims, 2 Drawing Figures

SERIAL ADIABATIC METHANATION AND STEAM REFORMING

BACKGROUND OF THE INVENTION

1. Field of the Invention

This invention relates to the production of synthetic fuels and is particularly concerned with a process wherein a reactant gas comprising carbon oxides and hydrogen is methanated to produce a substitute pipeline gas having a heating value of about 900 to 1000 BTU per standard cubic foot.

2. Description of the Prior Art

In the fixed bed catalytic methanation of gases containing carbon monoxide and hydrogen, the reaction between the carbon monoxide and hydrogen initiates generally at 400° F. to 450° F. The reaction is very exothermic and, if not controlled within the reactor, can cause sintering of the catalyst, carbon deposition on the catalyst and/or thermal cracking of the product methane to carbon and hydrogen. Carbon formation through thermal cracking and/or carbon monoxide disproportionation in turn has a tendency to foul the catalyst bed.

Most prior art methanation catalysts, by the nature of their supports, are not hydrothermally stable when used on a continuous basis at temperatures in excess of 900° F. to 1000° F. Therefore, many adiabatic prior art processes are "lower temperature" processes and preserve the catalyst by limiting methanation to temperatures from about 550° F. to about 900° F. For example, most of these "lower temperature" methanation processes employ nickel catalysts which tend to deactivate at 900° F.

Also, it is important that the gas enter at the lowest inlet temperature which will give an acceptable initiation reaction rate and still prevent the formation of a carbonyl compound which can occur through the reaction of the carbon monoxide with the catalyst at temperatures below proper operating temperatures.

To overcome some of these problems caused by overheating or carbonyl formation in these "lower temperature" methanation processes, extensive recycle streams are used as a diluent to absorb some of the exothermic heat evolved. Additional measures for avoiding too high temperatures in the reactor include cooling of the catalyst bed or of the reaction gases. For example, direct cold gas recycle and internal cooling of the reactor by heat transfer surfaces within the bed are recognized methods by which temperature controls may be effected. Local heating is difficult to avoid when using the latter and the building of internal exchange surfaces tends to be expensive. The hot gas recycle and direct cold gas recycle methods, on the other hand, require high recycle ratios. As a consequence, large pressure drops through the catalyst beds occur and the requirements for compressor power and stricter design specifications increase proportionately, hence increasing compression construction costs.

There is also a "higher temperature" prior art adiabatic methanation process which limits methanation temperatures between 900° F. and 1600° F. to preserve activity of the steam-hydrocarbon reforming catalyst employed therein. Below about 900° F., this "higher temperature" catalyst is essentially non-functional for methanation. Consequently, in order to initiate the exothermic methanation and water-gas shift reactions, the temperature of the steam-reactant gas feed stream fed to the first primary wet reactor must be above about 900° F. This "higher temperature" methanation process eliminates the disadvantages associated with "lower temperature" processes, i.e., the need to recycle product gases or introduce other gas streams for the purpose of diluting the reactants to control temperature, and in addition, it generates high pressure steam which may be used to serve other process needs.

However, preheating the steam-reactant gas feed stream fed to the first primary wet reactor to a temperature above about 900° F. requires the expenditure of large amounts of heat energy and/or the use of equipment having extensive heat transfer surfaces and materials of construction which will withstand the high temperatures and pressures employed to superheat steam and/or the feed stream. Moreover, there is the disadvantage that during preheating at temperatures above about 500° F., carbon may be deposited on heat exchange surfaces.

SUMMARY OF THE INVENTION

It is an object of the invention to provide a process for the production of methane from a reactant gas comprising $H_2$ and CO wherein essentially stoichiometric conversion of carbon oxides to methane is obtained and the exothermic reaction between CO and $H_2$ is controlled without the need of expensive internally cooled surfaces or high recycle ratios. Another object of the invention is to provide a process for the production of methane from a reactant gas comprising $H_2$ and CO wherein the catalyst damage by low or high temperatures is prevented with a minimum of investment and operating costs. Still another object is to provide a "hybrid high temperature" process for producing methane wherein the danger of carbon formation during preheating of the reactant gas is essentially eliminated. An additional object of this invention is to provide a methanation process which provides greater conversion to methane in the first primary wet reactor than provided by a "higher temperature" methanation process.

These and other objects of the invention are obtained by an improved process for the production of methane from mixtures of carbon oxides and hydrogen. In its broadest aspect, the invention relates to a process for the production of methane from a reactant gas comprising $H_2$ and carbon oxides in at least two primary, and at least one secondary wet, fixed bed, adiabatic, catalytic reaction zones in serial arrangement, wherein a cooling zone is provided between each secondary zone and between the last primary reaction zone and the first secondary reaction zone, the effluent gas from each primary reaction zone except the last zone being passed into the succeeding primary reaction zone, which process comprises:

a. introducing a first feed stream comprised of steam and said reactant gas into the first of said primary reaction zones at a first inlet temperature above about the minimum initiation temperature of a first catalyst situated therein, said first catalyst being hydrothermally stable from said first inlet temperature to a first outlet temperature between about 1100° F. and about 1200° F., the amount of steam in said first feed stream being sufficient to prevent both (1) carbon formation on the catalyst in each of said reaction zones and (2) overheating of the said first catalyst;

b. adiabatically reacting said first feed stream in the first primary reaction zone from said first inlet temperature to said first outlet temperature to produce an effluent gas;

c. introducing a second feed stream comprised of said reactant gas and the effluent gas from the first primary reaction zone into the second primary reaction zone at a second inlet temperature above about 900° F., the minimum initiation temperature of a second catalyst situated therein, said second catalyst being a steam-hydrocarbon reforming catalyst which is hydrothermally stable from said second inlet temperature to a second outlet temperature between about 1250° F. and about 1600° F.;

d. adiabatically reacting said second feed stream in said second primary reaction zone from said second inlet temperature to said second outlet temperature to produce an effluent gas;

e. repeating steps c and d in each succeeding primary reaction zone with a feed stream comprised of said reactant gas and the effluent gas from the preceding primary reaction zone;

f. introducing the effluent gas from the last primary reaction zone and each succeeding secondary wet reaction zone into one of said cooling zones wherein its temperature is regulated from an outlet temperature below about the maximum operating temperature of the catalyst in the preceding reaction zone to an inlet temperature above about the minimum initiation temperature of the catalyst in the succeeding reaction zone the catalyst in each secondary wet reaction zone being the same catalyst employed in the first primary reaction zone;

g. adiabatically reacting the cooled effluent gas of step f in the succeeding secondary, wet reaction zone to produce a produce gas rich in methane having a temperature below about the maximum operating temperature of the catalyst in the last of said secondary, wet reaction zones; and h. condensing a substantial portion of the steam present in said product gas to water which is removed from said product gas.

Further methanation of the product gas may be conveniently accomplished in a series of conventional secondary dry methanation zones as described subsequently.

By "reactant gas" as used throughout the specification is meant an essentially sulfur-free gas comprising hydrogen and carbon oxides. By an "essentially sulfur-free gas" as used throughout the specification is meant a gas in which sulfur and its compounds are not present or have been removed to a level of no more than about 1 ppm calculated as volumes of $H_2S$ per volume of reactant gas.

By "primary" methanation reaction zone or reactor as used throughout the specification is meant a reactor which receives for methanation at least some reactant gas which has not previously been methanated. By "secondary" methanation reaction zone or reactor is meant a reaction zone or reactor which receives for methanation a reactant gas which has previously been subjected to methanation at least once.

By "dry" reaction zone as used throughout the specification is meant a reaction zone wherein a feed stream which contains up to about 10 mole percent water preferably up to about 4 mole percent water, is subjected to methanation. By "wet" reaction zone is meant a reaction zone wherein a fed stream which contains more than about 12 but less than about 80 mole percent water, preferably more than about 16 but less than about 50 mole percent water, is subjected to methanation. Reactor and reaction zone are interchangeably used throughout the specification.

According to the process of this invention, the first primary reaction zone operates to provide substantial conversion to methane as well as an economical means to preheat the second feed stream introduced into the second primary reaction zone to a temperature above about the minimum initiation temperature of the catalyst in the second primary reaction zone. This is accomplished by employing a methanation catalyst in the first primary reaction zone having both high activity and hydrothermal stability over a wide temperature range in carrying out the desired conversions. This first methanation catalyst should initiate the methanation reaction at a temperature above about 550° F.

Moreover, the maximum operating temperature at which the first stage catalyst provides a satisfactory useful life must be at least 100° F. above about the initiation temperature of the catalyst employed in the second primary methanation zone. It is desirable to maximize the ratio of reactant gas fraction to effluent gas in the feed stream reacted in each primary reaction zone subsequent to the first one. This maximization is influenced in the first primary reaction zone by the maximum operating temperature of the first stage catalyst and the minimum initiation temperature of the second stage catalyst. The temperature of the first effluent gas in excess of the initiation temperature of the second stage catalyst is used to elevate the temperature of the second feed stream to above about the minimum initiation temperature of the second stage catalyst.

The catalyst in the second and any subsequent primary methanation reaction zone can operate at a temperature range between about 900° F. and about 1600° F. The hot effluent gas from the first and each succeeding primary reaction zone except the last primary zone, is admixed proportionately with reactant gas to provide the feed stream for each succeeding reaction zone. The reactant gas is typically at a temperature between about 200° F. and about 500° F., preferably at a temperature between about 250° F. and about 450° F. The feed stream fed to each reaction zone is at a temperature above about the initiation temperature of the catalyst situated therein.

All of the heat transfer surfaces involved in preheating the steam and reactant gas can be operated at temperatures well below the initiation temperature of the catalysts situated in the primary reaction zones except the first primary zone. Steam is added to the first feed stream at such temperature and pressure that condensation from the mixture does not occur.

Primary methanation in the process of this invention is carried out in a reaction system comprised of a series of two or more fixed-bed, adiabatic catalytic reactors. Heat is removed from the effluent gas of the last primary and each secondary reactor by passing the effluent gas through a cooling zone as it passed from one such reactor to the succeeding reactor. The cooling zone may be a conventional heat exchanger, for example, a waste heat boiler.

The catalyst employed in the first primary reactor must be capable of initiating methanation at a temperature of about 550° F. and operating at temperatures up to about 1200° F. Commercial methanation catalysts used in "lower temperature" methanation processes will not work. These commercial catalysts include, for example, the metals, iron, cobalt, nickel, or noble metal, e.g. platinum, palladium, rubidium and ruthenium, in the elemental or combined state, e.g. their oxides, sulfides or other inorganic form.

In conventional "lower temperature" methanation catalysts, a maximum temperature in excess of about 1000° F. causes rapid aging and rapid deactivation of the catalyst. Some conventional nickel methanation catalysts are not suitable for the process of this invention wherein large quantities of steam are injected with the reactant gas to the first primary reaction zone. It is known that the specific nickel surface area of conventional methanation catalysts, a very sensitive measure of methanation activity, decreases at an increasing rate with increases in the ratio of $H_2O/H_2$ in the feed stream being reacted or with the temperature.

It has been found, however, that catalysts of the type disclosed in U.S. Pat. No. 3,988,263, which disclosure is incorporated herein by reference, may be advantageously employed in the first primary reaction zone in the process of this invention. In U.S. Pat. No. 3,988,263, there are disclosed catalysts having a high degree of thermal stability, comprising alumina and nickel. The catalysts are prepared from aqueous solutions containing a dissolved aluminum salt, a salt of divalent nickel, and a delayed precipitant which hydrolyzes to form ammonia and carbon dioxide, such as urea. With all components in homogeneous solution at a relatively low pH and temperature, the solution is heated to a temperature sufficient to hydrolyze the delayed precipitant with resultant liberation of ammonia and carbon dioxide homogeneously throughout the solution, until the pH of the solution rises sufficiently to effect coprecipitation of the metal salts as hydroxides and/or carbonates. The resulting coprecipitate is then recovered, washed, dried, shaped and calcined in conventional fashion to obtain a final product which is very active, and displays much greater hydrothermal stability than corresponding prior art catalysts prepared by nonhomogeneous coprecipitation with alkaline, ionic reagents such as sodium carbonate, ammonium hydroxide, or ammonium carbonate. A preferred catalyst is a coprecipitated nickel oxide-alumina catalyst containing about 47 weight percent of nickel oxide made according to the techniques disclosed in Example VIII of U.S. Pat. No. 3,988,263.

It is believed that other suitable catalysts for the first reaction zone include those disclosed in U.S. Pat. No. 3,988,262, which disclosure is also incorporated herein by reference. In U.S. Pat. No. 3,988,262, there are disclosed catalysts consisting essentially of nickel and porous support material containing alumina, the components being evenly distributed amongst each other, in which the content of nickel is from 15 to 40% by weight, calculated as nickel oxide, of the total catalyst and zirconia and alumina are present in a ratio of from 0.05 to 2.0 parts by weight of zirconia per part by weight of alumina and which catalyst has been prepared by the sequential steps of (a) preparing an aqueous solution of a nickel salt and containing, in at least partly dissolved state, aluminum and zirconium compounds thermally decomposable to the oxides, (b) precipitating substantially all metal ions from said aqueous solution by the addition of a base, (c) isolating and drying the precipitated metal compounds mixed with any undissolved compounds present in the system formed in step (b), (d) converting the thus-formed mixture of compounds into a mixture of the corresponding oxides by calcination at temperatures between 300° and 500° C., (e) working up the thus-formed oxides mixture into particles of any desired shape and size, (f) subjecting the shaped particles to a firing temperature of between 800° and 1100° C. for two to ten hours and (g) subsequently at least partially reducing the nickel oxide present in the first particles into metallic nickel.

For the second and any subsequent primary reaction zones, the catalyst employed must be capable of: (1) operating continuously at high inlet temperatures of above about 900° F. with outlet temperatures up to about 1600° F. without rapid catalyst degradation, (2) handling a reactant gas of essentially any composition, insofar as hydrogen and the carbon oxides are concerned; (3) handling gas streams of high concentrations of carbon oxides without the need to cool the catalyst itself and with only the need to provide a feed stream temperature for the next reactor at an inlet temperature above about 900° F.; (4) simultaneous methanation and shift conversion eliminating the requirement for a separate water-gas shift reactor in advance of a first wet methanation zone. By use of such a catalyst, there is no need to recycle product gas or introduce other gas streams for the purpose of diluting the reactants to control temperature.

The steam-hydrocarbon reforming catalyst employed in the second and any subsequent primary reaction zone comprises from about 5 to about 35% by weight of iron, cobalt or nickel or combinations thereof on a temperature stabilized, ceramic alumina support. Thermal stability is induced by heat treating the support by calcining and the like at a temperature above 1600° F. prior to depositing the metal on the support. The preferred supports are of relatively low surface area and the alumina content is preferably maximized to prevent other constituents such as silica from being volatilized and contaminating heat exchange surfaces. Catalysts with the preferred supports are known in the art for the steam reforming of methane and other hydrocarbons.

Reactant gas precursors are comprised of carbon monoxide and hydrogen and may include, as well, other gases such as methane, ethane, nitrogen, carbon dioxide, argon, and water vapor. The reactant gas precursor is stripped of tar and particulate matter and optionally subjected to shift conversion to obtain $H_2/CO$ ratio of about 3–3.5/1. The shift reaction does not ordinarily go to completion. The degree of completeness is limited by equilibrium, which is, in turn, dependent on the temperature and the concentration of the active species (CO, $H_2O$, $CO_2$ and $H_2$). By an appropriate choice of process conditions, a composition having the desired ratio of $H_2$ to CO may be obtained.

After optional shift conversion of the reactant gas precursor, it will generally contain excess $CO_2$ and steam and may also contain deleterious impurities such as sulfur compounds. Any excess $CO_2$ and water are hence removed. Sulfur compounds must be removed to residuals substantially about 1 ppm as defined previously herein, and preferably less than about 0.2 ppm to protect the catalysts employed in the methanation reactors which are poisoned by sulfur.

In accordance with the process of this invention, the composition of the gases entering the reactors is adjusted to a content of steam, carbon oxides and hydrogen which when reacted will produce an amount of heat insufficient to raise the gas temperature above the maximum operating temperature of the catalyst employed therein. Thus, in the first reactor or reaction zone of the system, a first feed stream comprised of reactant gas and steam is used with a steam, carbon oxides and hydrogen content sufficient to raise the temperature of the first feed stream from an inlet gas temperature greater than the minimum initiation temperature of the catalyst in the first reactor to an outlet temperature no greater than the maximum operating temperature of the catalyst in the first reactor and at least 150° F. greater than the initiation temperature of the catalyst in the second reactor.

After adiabatic reaction in the first primary reactor, the first effluent gas is deficient in $H_2$ and CO. Hence, if the first effluent gas were to be reacted by itself in the second primary reactor, a temperature rise much lower than that in the first primary reactor would result. This would be due to the lower equilibrium temperature reached since the heat of reaction was removed in the first primary reactor. The reactant gas is, of course, rich in $H_2$ and CO. Admixing the reactant gas with the first effluent gas therefore enriches the $H_2$ and CO content of the first effluent gas.

The inlet temperature for each of the primary reactors will be at or above the initiation temperature of the catalyst in each reactor. Carbon formation is prevented in each primary reactor by adding steam to the reactant gas passed into the first primary reactor in an amount sufficient to prevent carbon formation therein and in each subsequent primary reactor. The steam added to the first primary reactor plus the steam generated in each subsequent wet methanation reactor is passed, along with the effluent gas into the succeeding wet methanation reactor.

DESCRIPTION OF THE PREFERRED EMBODIMENTS

Figure 1:
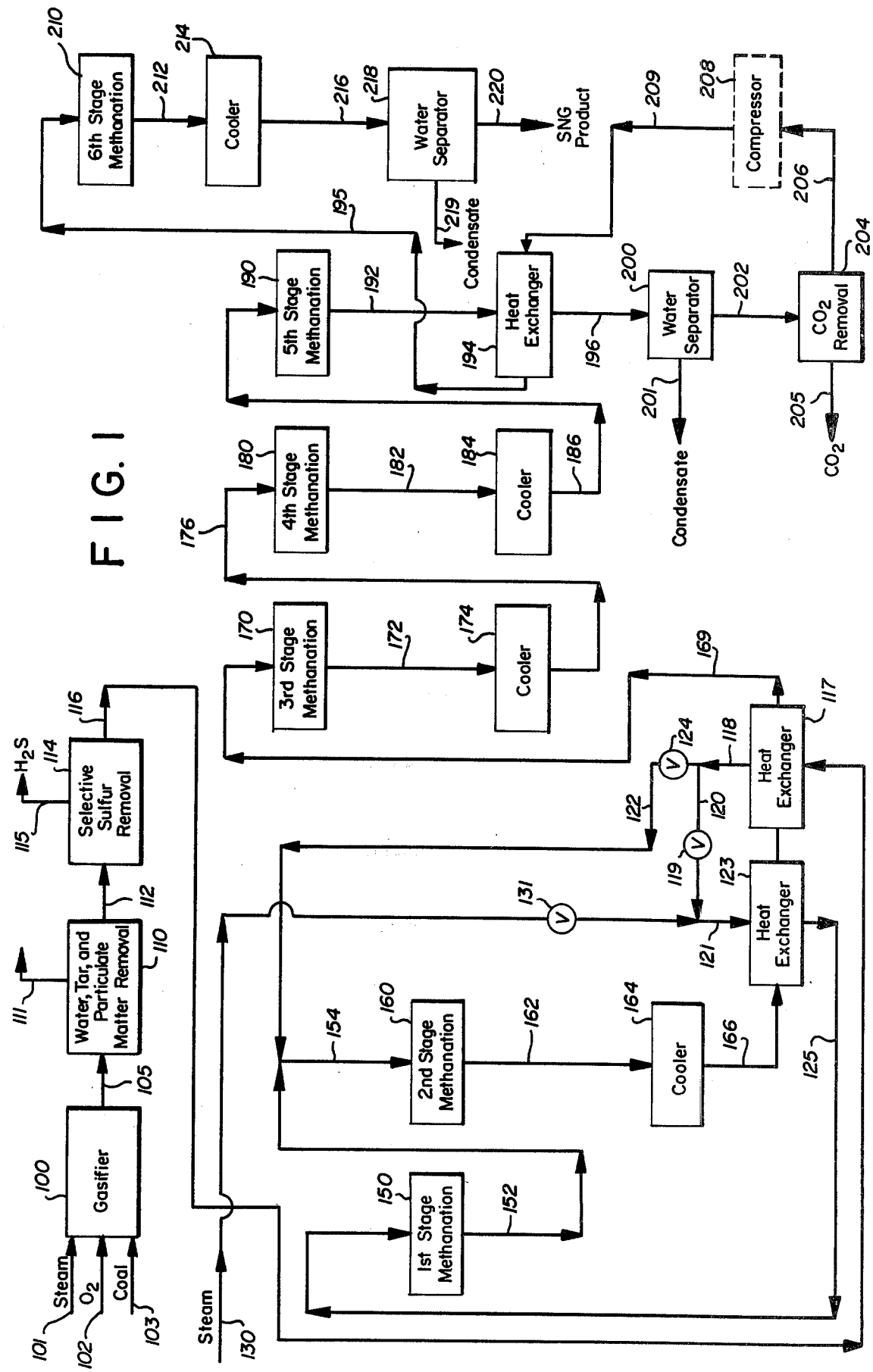
FIG. 1 is a schematic flow sheet illustrating an embodiment of the invention.
Figure 2:
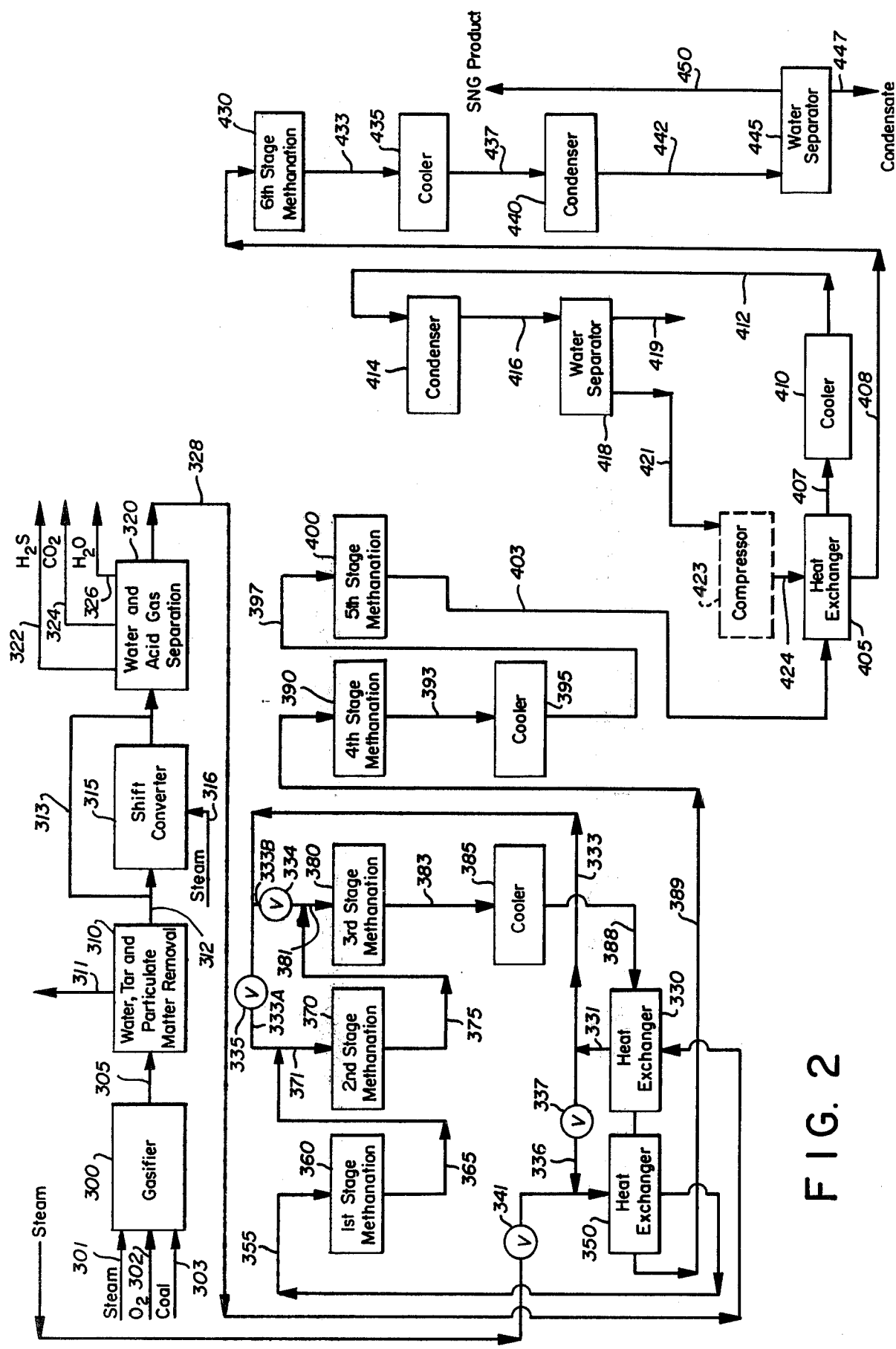
FIG. 2 is a schematic flow sheet illustrating another embodiment of the invention.

According to the present invention, there is essentially provided a process for the production of a substitute pipeline gas from a reactant gas. The process is carried out in a manner which avoids potential carbon formation and deposition on catalysts employed in the methanation stages. FIGS. 1 and 2 are schematic flow diagrams which illustrate processes in which raw synthesis gas produced by gasification of coal is methanated in the presence of a catalyst. It will be understood that the invention is not restricted to the methanation of synthesis gases produced from coal and is equally applicable for the upgrading of synthesis gas and similar mixtures of carbon oxides and hydrogen derived from shale oil, heavy crude oils, petroleum coke, residual petroleum fractions, naphtha and the like. However, for purposes of illustrating the invention, both FIGS. 1 and 2 show coal gasification reactors.

In the gasifier reactor, synthesis gas comprising principally hydrogen, carbon monoxide, carbon dioxide, water vapor, methane, and one or more members of the group consisting of nitrogen, argon, carbonyl sulfide, and hydrogen sulfide, as well as entrained particulate carbon is produced by the reaction of a hydrocarbonaceous fuel by partial oxidation with oxygen and/or steam at temperatures between about 1200° F. and about 2500° F. and at pressures between 30 psi to about 2000 psi or greater.

Typical gasification processes are the Bi-Gas Process of Bituminous Coal Research, Inc., the Synthane Process of the Bureau of Mines and the COGAS Process of FMC Corporation. Older processes which have been employed commercially for the manufacture of low BTU gas include the Koppers-Totzek process of the Koppers Company and the Lurgi Process of the Lurgi Gesellschaft of Frankfurt, Germany.

The effluent gas from the gasification reactor may have the following gas composition in mole percent:

TABLE I

| RAW SYNTHESIS GAS COMPOSITION | |
|---|---|
| Component | Mole Percent (Dry Basis) |
| $H_2$ | 20–59 |
| CO | 10–70 |
| $CO_2$ | 5–40 |
| $H_2S$ | 0–2.0 |
| $CH_4$ | 0–25 |
| COS | 0–0.1 |
| $N_2$, Ar | 0–2 |

For purposes of illustration, FIG. 1 shows a Koppers-Totzek gasifier 100 into which coal, stean and oxygen are fed via lines 103, 101 and 102, respectively and FIG. 2 shows a Lurgi type gasifier 300 into which coal, steam and oxygen are also fed via lines 303, 301, and 302, respectively.

Referring to FIG. 1, the effluent gas stream 105 from gasifier reactor 100 is passed into scrubbing zone 110 to remove tar, particulate carbon and any other entrained solids via line 111. Well known scrubbing techniques may be employed to remove tar and particulate material such as scrubbing effluent gas stream 105 with a scrubbing fluid comprising oil, water or both at high pressures and temperatures. It is beneficial to avoid cooling of the effluent gas stream 105 so as to retain water in the gas stream 112.

When required, additional scrubbing may be provided to supplement the previously mentioned gas scrubbing. For example, the gas stream may be washed with a liquid hydrocarbon by means of a scrubbing nozzle or venturi scrubber, such as described in Perry's Chemical Engineers' Handbook Fifth Edition, McGraw Hill 1973, Pages 1890–1892. The process gas stream leaves the top of the scrubbing tower substantially free of particulate material and at a temperature in the range of about 400° F. to 650° F.

$H_2S$ may be removed from the process gas stream 112 in selective sulfur removal zone 114 via line 115. For example, the gas cooled to 100° F. to 200° F. may be physically or chemically absorbed with alkaline absorbents (solvents), such as n-methyl pyrrolidone, triethanolamine, propylene carbonate, or alternatively with methyl alcohol, or promoted alkali carbonates such as hot potassium carbonate. Methane should be substantially insoluble in the solvent selected.

Hydrogen sulfide and other sulfur bearing gases, together with part of the carbon dioxide, are absorbed selectively by the solvent. When necessary, final cleanup may be accomplished by passing the process gas through iron oxide, zinc oxide or activated carbon to remove residual traces of $H_2S$ or organic sulfide. If the sulfur compounds are present in quantities higher than 50–100 ppm, a selective process for extracting sulfur is preferable so as to make possible the recovery of sulfur in a stream of sufficient concentration ot permit conversion to sulfur or sulfuric acid in a suitable process. For example, the Claus process may be used to produce elemental sulfur from $H_2S$ as described in Kirk-Othmer Encyclopedia of Chemical Technology, Second Edition, Volume 19, John Wiley, 1969, page 352. If the sulfur compounds are present in quantities less than 50 ppm, it is usually more economic to absorb the sulfur on zinc oxide or similar absorbents which can be disposed of by batch removal from the system. A combination of sulfur extraction and final cleanup by absorption on zinc oxide may also be used. This part of the technology is well known and selection of a particular route is governed mainly by economics.

Reactant gas stream 116 may optionally be pressurized in compression zone (not shown) before being preheated in heat exchanger 117 to a temperature such that after portions of the preheated reactant gas 116 are mixed with cooled effluent gas from the first primary reaction zone, the mixture of first cooled effluent gas and preheated reactant gas fraction will have a temperature high enough to initiate reaction in reaction zone 160. Generally, reactant stream 116 is preheated in heat exchanger 117 to a temperature of about 200° F. to about 500° F., preferably to a temperature of about 250° F. to about 450° F.

Preheated reactant gas 118 is split into a number of fractions depending on the number of primary reaction zones desired. In the embodiment illustrated in FIG. 1, two primary reaction zones for methanation are shown and hence the preheated reactant gas 118 is split into fractions 120 and 122. Steam flow rate through line 130 is controlled by valve 131. The flow rate of the first feed gas fraction through line 120 is controlled by valve 119. And the flow of the second reactant gas fraction through line 122 is controlled by valve 124.

Steam is provided at a temperature between about 330° F. and about 800° F. The steam via line 130 and valve 131 is admixed with the first reactant gas fraction via line 120 and valve 119. The resultant mixture, via line 121, is preheated in heat exchanger 123 and fed through line 125 into reaction zone 150. The inlet temperature for the mixture introduced into reaction zone 150 should be between about 550° F. and 700° F., preferably between about 550° F. and 600° F. The ratio of steam to reactant gas fraction 120 should be sufficient to prevent the development of excess temperature in methanation reaction zone 150. Steam is the primary temperature moderator in reaction zone 150 although the $H_2$ and carbon oxides content of reactant gas fraction 120 also contributes to temperature moderation in reaction zone 150. Methane is formed by the reaction of carbon oxides contained in the desulfurized synthesis gas fraction 120 with hydrogen in reaction zone 150.

In the system shown in FIG. 1, six methanation reactors of fixed bed type designated by reference numerals 150, 160, 170, 180, 190 and 210 and seven heat exchangers or similar heat recovery units designated by reference numerals 117, 123, 164, 174, 184, 194 and 214 are provided. The reactors shown are of the type in which the gas moves downwardly through catalyst particles supported on trays or similar internal supporting elements by fixed bed units of other types can also be used.

Among the constituents of the synthesis gas, CO and $CH_4$ are precursors of carbon. Carbon formation can be prevented by lowering the partial pressures of CO and $CH_4$ below those predicted by their respective carbon-forming equilibria. Steam is added only to the feed stream for the first primary reaction zone 150. Steam is employed to reduce partial pressures of CO and $CH_4$ in the reactant gas. Steam, in conjunction with moisture already in the reactant gas and the net quantity of water generated by the reactions, prevents carbon deposition in each methanation reaction zone.

Suitable catalysts for the first methanation zone 150 in FIG. 1 (and for methanation zones 360 and 390 of FIG. 2 as discussed subsequently herein) include methanation catalysts capable of operating at temperatures between 550° F. and about 1200° F. as previously described herein.

As the first feed stream passes through the catalyst mass in the first primary methanation reactor 150, temperature rises rapidly and approaches that for thermodynamic equilibrium achieved under adiabatic reaction conditions. The effluent gas temperature from the first methanation reactor 150 is between about 1100° F. and 1200° F. to obtain optimum conversion while preventing thermal cracking of the methane formed. The advantage of operating the first methanation reactor as high as about 1100° F. to about 1200° F. is it tends to maximize the amount of second reactant gas fraction that may be admixed with first effluent gas for methanation in the second methanation reactor 160.

The first stage effluent gas exiting from the first primary methanation zone 150 via line 152 is admixed with a second reactant gas fraction conveyed by line 122. The total feed stream in line 154 from lines 122 and 152 is at an inlet temperature sufficient to initiate reaction in reactor 160, the second primary stage.

The effluent gas temperature from the second methanation reactor 160 is between about 1200° F. and about 1600° F. This outlet temperature is lower than the outlet temperature obtained if the first methanation reaction zone 150 had been omitted. Consequently, improved conversion to methane and more favorable equilibrium is provided according to the process of this invention. Moreover, the outlet temperature achieved from the second methanation reactor 160 is sufficient so that heat may be economically recovered for preheating reactant gases and for steam generation.

The effluent gas from the second primary methanation zone 160 passes through line 162 into cooling unit 164 for cooling. In such cooling unit 164, the gas is passed in indirect heat exchange with water or other cooling fluid and steam or other hot fluid is recovered. Cooled second stage effluent gas exiting from cooler 164 via line 166 is passed through heat exchangers 123 and 118 for subsequent further cooling until it is at an inlet temperature sufficient to initiate reaction in reactor 170, the third methanation stage.

The amount of heat removed from the second effluent gas in heat exchangers 117 and 123 is predetermined by the amount of heat required to preheat the feed gas fractions fed to the primary methanation reactors 150 and 160. The temperature of the cooled effluent gas leaving heat exchanger 117 via line 169 is predetermined by the inlet temperature required for the first of the secondary methanation zones 170. This inlet temperature must be not more than about 100° F. above the initiation temperature of the catalyst situated in the reaction zone 170, so as to provide maximum temperature rise and conversion of the feed stream in the secondary reaction zone 170. Since the temperature of the second effluent gas leaving heat exchangers 117 and 123 is predetermined and the amount of heat removed in heat exchangers 117 and 123 is also predetermined, the amount of heat removed in cooling unit 164 is the difference between the heat content of the second effluent gas and the heat content of the reactant gas for methanation zone 170.

The third reactor 170 is a wet reaction zone and the first secondary reaction zone. The catalyst employed in the first secondary methanation zone 170 has the same operating characteristics as the catalyst employed in the first primary methanation zone 150. The effluent gas leaving the last of the primary methanation zones 160, is at a temperature of about 1200° F. to about 1600° F. Such a high temperature corresponds to an unfavorable equilibrium conversion to methane. Consequently, the temperature rise and hence the outlet temperature of the first secondary methanation zone will also be high, i.e., between about 1000° F. and about 1200° F. This compels the use of the same catalyst or a catalyst with the same operating characteristics as the catalyst employed in the first primary methanation zone 150. Reaction zones 170, 180 and 190 substantially complete the bulk of the methanation of the feed gas and their respective outlet temperatures are generally substantially below that of the primary reaction zones, e.g. zone 160 employing a steam-hydrocarbon reforming catalyst.

The equilibrium composition of the effluent gas from the second primary reactor 160, when reacted in the third reactor 170 at an inlet temperature, as previously described herein, will not provide as high an outlet temperature as resulted in primary reactor 160. The high content of reactive constituents, i.e. the $H_2$ and CO, formerly in the reactant gas, has been substantially depleted.

Although only two primary methanation reactors are illustrated in FIG. 1, more than two primary methanation reactors may be employed in the process of this invention. The advantage of using more than two primary methanation reactors is that the ratio of steam added to the feed stream for the first primary reactor to total reactant gas decreases as the number of primary methanation reactors is increased.

Effluent gases from the third and fourth methanation zones exit via lines 172 and 182, respectively. They are cooled in cooling units 174 and 184, respectively, to a temperature not more than about 100° F. above the minimum initiation temperature of the catalyst situated in the fourth and fifth methanation zones 180 and 190, respectively. This catalyst preferably is the same catalyst employed in the first primary reaction zone 150, but could be a commercial "lower temperature" catalyst provided the maximum temperature limitation of the catalyst employed would not be exceeded. Temperature rise in a given reactor is dependent on stream's approach to equilibrium gas composition and the composition of the inlet stream gas. For a given temperature rise, reactivity of the effluent gas fed to each succeeding secondary wet reactor can be calculated. Successive decrease in outlet temperatures from reactor to reactor would be expected in these secondary reactors.

The cooled effluent gases pass into the fourth and fifth methanation zones 180 and 190, via lines 176 and 186, respectively, and are reacted therein. In a similar manner the effluent gas from the fifth methanation zone 190 passes via line 192 through heat exchanger 194 and is cooled as subsequently discussed.

Cooled effluent gas from heat exchanger 194 is passed via line 196 into water removal zone 200. Condensate water from the cooled gas is separated via line 201. The effluent gas stream from which most of the water has been condensed contains excess quantities of carbon dioxide and is fed via line 202 into $CO_2$ removal zone 204. In $CO_2$ removal zone 204, $CO_2$, in excess of the amount which with the residual CO can stoichiometrically react with the residual $H_2$, is removed via line 205.

The effluent gas from which excess $CO_2$ has been removed is fed via line 206 into optional compressor 208 for optional compression to a pressure greater than the specified delivery pressure for introduction into a pipeline network for use as substitute natural gas. The optionally compressed gas is passed via line 209 into heat exchanger 194. A predetermined amount of heat is exchanged in cooling the fifth effluent gas in order to raise the temperature of the optionally compressed gas in line 209 to the initiation temperature of the catalyst situated in the final methanation zone(s) 210.

The preheated gas from heat exchanger 194 is introduced via line 195 into the sixth methanation zone 210, a dry methanation zone. Therein, reaction of the residual reactive components raises the heating value of the gas, after drying, to about 900–1000 BTU/SCF. The catalyst employed in the sixth methanation zone 210 may be a commercial "lower temperature" methanation catalyst. Subsequent to this methanation zone 210, the effluent gas is passed into a cooling unit 214 via line 212 for cooling to ambient temperature. After cooling, the gas is passed via line 216 into water removal zone 218. Condensate is removed via line 219 and effluent gas essentially having a heating value of about 900–1000 BTU/SCF is produced.

As stated previously herein, FIG. 2 shows a Lurgi type gasifier 300 into which coal, steam and oxygen are fed via lines 303, 301 and 302, respectively. The effluent gas stream 305 from gasifier reactor 300 is passed into scrubbing zone 310 to remove tar, particulate carbon and other entrained solids via line 311 essentially described previously herein with respect to scrubbing zone 110.

A portion of the cleaned reactant gas presursor leaving scrubbing zone 310 via line 312 is fed into shift converter 315. Therein, its carbon monoxide is reacted with steam (fed into shift converter via line 316) to produce carbon dioxide and additional hydrogen by means of the water-gas shift reaction. In FIG. 2, part of the reactant gas precursor is shown as bypassing shift converter 315 via line 313. By an appropriate choice of process conditions well known in the art, it is possible to arrive at a gas composition after shift conversion wherein the ratio of $H_2$ to CO is substantially in excess of about 3 to 1. The overshifted gas product in line 319 is admixed with the unreacted by-passed remainder via line 313 to provide a reactant gas precursor composition having a ratio of $H_2$ to CO of about 3 to 1. Alternatively, the bypass line 313 may be necessary if the water gas shift reaction is conducted in shift converter 315 so to initially produce a reactant gas precursor composition having the desired $H_2$/CO ratio of about 3–2.5 to 1.

The shifted reactant gas precursor is then introduced into water and acid gas separation zone 320 wherein $H_2S$ is removed via line 322, $CO_2$ is removed via line 324 and $H_2O$ is removed via line 326. $H_2O$ is removed by condensation. $H_2S$ and $CO_2$ are selectively removed by such known processes as Rectisol, hot carbonate, and the like.

In the embodiment illustrated in FIG. 2, three primary reaction zones for methanation are shown and hence the preheated reactant gas 331 is split into fractions 333A, 333B and 336. Each fraction is apportioned to control temperature rise in each primary methanation reaction zone. Steam flow rate through line 340 is controlled by valve 341. The flow rate of the first, second and third reactant gas fractions through line 336, 333A and 333B is controlled by valves 337, 335 and 334 respectively.

Steam via line 340 is admixed with a first reactant gas fraction via line 336. The resultant feed stream is preheated in heat exchanger 350 and fed through line 355 into reaction zone 360. Operation of the first reaction zone 360 is as described previously herein with respect to reaction zone 150, including the use in zone 360 of the same catalyst or a catalyst having the same operating characteristics as the catalyst employed in zone 150.

After adiabatic methanation of the first feed stream at a temperature from about 550° F. to about 1200° F., the first stage effluent gas conveyed by line 365 is admixed with a second reactant gas fraction conveyed by line 333A. The second feed stream in line 371 is at an inlet temperature sufficient to initiate reaction in reactor 370, the second primary stage. The second feed stream is adiabatically methanated in the second reaction zone at a temperature from about 900° F. to about 1600° F. essentially as described previously herein with respect to reaction zone 160.

Effluent gas from the second primary reaction zone 370 is conveyed via line 375 and admixed with a third reactant gas fraction via line 333B and valve 334 to raise the temperature of the third feed stream to a temperature sufficient to initiate reaction in the third primary reaction zone 380. The third feed stream is fed into the third primary reaction zone 380 via line 381 and adiabatically methanated essentially as described herein with respect to the second primary reaction zone 370.

The effluent gas from the third primary methanation zone 380 passes through line 383 into cooling unit 385 for cooling essentially as described previously herein with respect to cooler 164. Cooled third stage effluent gas exiting from cooler 385 via line 388 is passed through heat exchangers 330 and 350 for subsequent further cooling until it is at an inlet temperature sufficient to initiate reaction in reactor 390, the fourth methanation stage.

The amount of heat removed from the third effluent gas in heat exchangers 330 and 350 is predetermined by the amount of heat required to preheat the reactant gas fractions fed to the primary methanation reactors 360, 370 and 380. The temperature of the cooled effluent gas leaving heat exchanger 350 via line 389 is predetermined by the inlet temperature required for the first of the secondary methanation zones 390. This inlet temperature must not be more than about 100° F. above the initiation temperature of the catalyst situated in the reaction zone 390 to provide maximum temperature rise and conversion of the feed stream in the secondary reaction zone 390. Since the temperature of the third effluent gas leaving heat exchangers 330 and 350 is pedetermined and the amount of heat removed in heat exchangers 330 and 350 is also predetermined, the amount of heat removed in cooling unit 385 is the difference between the heat content of the third effluent gas and the heat content of the feed stream for reaction zone 390.

The fourth reactor 390 is a wet reaction zone and the first secondary reaction zone. The catalyst in the second methanation zones is the same catalyst employed in the first primary methanation zone 360. Reaction zones 390, 400 and 430 substantially complete the bulk of the methanation of the reactant gas and their respective outlet temperatures are generally substantially below that of the primary reaction zones 370 and 380 employing a steam-hydrocarbon reforming catalyst.

Effluent gas from the fourth methanation zone 390 exits via line 393 and is cooled in cooling unit 395 to the initiation temperature of the catalyst situated in the fifth methanation zone 400. This catalyst is the same catalyst employed in the fourth reaction zone 180, as described previously herein. The cooled effluent gas passes into the fifth methanation zone 400 via line 397 and is reacted therein. In a similar manner, the effluent gas from the fifth methanation zone 400 passes via line 403 through heat exchanger 405 then via line 407 through cooling unit 410 and is cooled as subsequently discussed.

Cooled effluent gas from cooling unit 410 is passed via line 412 into condenser 414 for further cooling. Subsequently, the gas is fed via line 416 into water separator 418. Condensate is removed via line 419. The effluent gas stream from which most of the water has been condensed, for example, to less than about 4 mole percent water, is fed via line 421 into optional compressor 423 for optional compression as described previously herein with respect to compressor 208. The optionally compressed gas is passed via line 424 into heat exchanger 405. A predetermined amount of heat is exchanged in cooling the fifth effluent gas in order to raise the temperature of the compressed effluent gas in line 424 to the initiation temperature of the catalyst situated in the final methanation zone(s) 430.

The preheated gas from heat exchanger 405 is introduced via line 408 into the sixth methanation zone 430, a dry methanation zone. The catalyst employed therein and operation of this reaction zone is as described previously herein with respect to reaction zone 210. Subsequent to this methanation zone 430, the effluent gas is passed into a cooling unit 435 via line 433 for cooling to ambient temperature. After cooling, the gas is passed via line 437 into condenser 440 and then via line 442 into water separator 445. Condensate is removed via line 447 and effluent gas essentially having a heating value of about 900–1000 BTU/SCF is available via line 450.

The following example is intended to illustrate the invention without limiting it in any manner.

EXAMPLE 1

A typical embodiment of the process of this invention is set forth below in Table I illustrated by a material balance, obtained by carrying out the embodiment of the process shown in FIG. 1. The block diagram of FIG. 1 represents the main process steps. The material balance specifically applies to the process steps as numbered on FIG. 1.

The material balance computations are based on production of 100 pound moles per hour of a high heating value substitute natural gas from a coal gasifier effluent, corresponding in composition to that from a Koppers-Totzek type gasifier.

The requisite quantity of steam via line 130 is injected with the reactant gas fraction into the first primary methanation stage 150 via line 125 to hold the temperature rise in that stage to below about 1200° F. Product gas from the first primary stage is mixed with the quantity of fresh reactant gas fraction which will produce an inlet temperature of above about 900° F. for the second stage. An inlet temperature of 550° F. and outlet temperatures ranging up to 1200° F. for the first, third, fourth, fifth and sixth stages using the following catalyst has been found to provide long catalyst life, under the conditions indicated in Table II below.

The catalyst employed for the first primary stage was obtained from Union Oil Company of California, Brea, California. It was found to be hydrothermally stable for adiabatic methanation between the temperatures of about 550° F. and about 1200° F. It is believed to be a coprecipitated nickel oxide-alumina catalyst containing about 47 weight percent of nickel oxide made according to the techniques disclosed in Example VIII of U.S. Pat. No. 3,988,263.

The catalyst employed for the second primary stage is a steam-hydrocarbon reforming catalyst. Any number of commercial steam-hydrocarbon reforming catalysts are suitable. Examples of suitable steam-hydrocarbon catalysts include: Girdler G-56A, 15% by weight nickel and Girdler G-56B, 25% by weight nickel (commercially available from Girdler Chemical, Inc., Louisville, Kentucky) and the C11 series of steam-hydrocarbon reforming catalysts containing 16-25% by weight nickel e.g. C11-2-03 (16% by weight nickel); C11-2-S-04 (25% by weight nickel); and C11-4-03 (16% by weight nickel), commercially available from Catalysts and Chemicals, Inc., Louisville, Kentucky.

Only two primary stages are required for a Kopper-Totzek type feed. The reactant gas which forms the feed stream to the second stage is preheated to 400° F. The steam to total reactant gas ratio of 0.61 is a near minimum for prevention of carbon deposition in the secondary methanation stages.

As stated previously herein, Table I summarizes the compositions and flow data for streams identified by the numerals of their conveying lines in FIG. 1 as follows:

TABLE I

| STREAM NO. | MATERIAL BALANCE PRODUCTION OF SNG | | | | | | | |
|---|---|---|---|---|---|---|---|---|
| | 130 | 116 | 125 | 152 | 154 | 162 | 169 | 172 |
| COMPONENT (M %) | | | | | | | | |
| INERTS | | 1.03 | 0.357 | 0.383 | 0.667 | 0.714 | 0.714 | 0.800 |
| $H_2$ | | 33.26 | 11.512 | 16.904 | 24.078 | 24.636 | 24.636 | 15.016 |
| $H_2O$ | 100.0 | — | 65.387 | 58.275 | 32.716 | 29.109 | 29.109 | 33.164 |
| CO | | 59.39 | 20.556 | 2.659 | 27.540 | 16.511 | 16.511 | 7.016 |
| $CO_2$ | | 6.22 | 2.153 | 18.018 | 12.844 | 23.194 | 23.194 | 31.450 |
| $CH_4$ | | 0.10 | 0.035 | 3.760 | 2.155 | 5.836 | 5.836 | 12.554 |
| FLOW RATE (LB.MOLES/HR.) | 68,480 | 112,400 | 104,730 | 97,480 | 173,620 | 162,180 | 162,180 | 144,760 |
| TEMPERATURE (° F) | — | — | 550 | 1200 | 900 | 1401 | 550 | 1189 |
| PRESSURE (PSIG) | — | — | — | 300 | — | 294 | — | 274 |
| STREAM NO. | 176 | 182 | 186 | 192 | 195 | 212 | 220 | |
| COMPONENT (M %) | | | | | | | | |
| INERTS | 0.800 | 0.866 | 0.866 | 0.893 | 3.981 | 4.094 | 4.218 | |
| $H_2$ | 15.016 | 6.065 | 6.065 | 1.291 | 5.756 | 0.525 | 0.541 | |
| $H_2O$ | 33.164 | 37.835 | 37.835 | 40.869 | 0.382 | 2.937 | — | |
| CO | 7.016 | 1.268 | 1.268 | 0.067 | 0.299 | 0.001 | 0.001 | |
| $CO_2$ | 31.450 | 36.245 | 36.245 | 37.059 | 1.215 | 0.131 | 0.135 | |
| $CH_4$ | 12.554 | 17.721 | 17.721 | 19.821 | 88.367 | 92.312 | 95.105 | |
| FLOW RATE (L.B. MOLES/HR.) | 144,760 | 133,720 | 133,720 | 129,690 | 29,090 | 28,280 | 27,450 | |
| TEMPERATURE (° F) | 550 | 949 | 550 | 684 | 500 | 597 | — | |
| PRESSURE (PSIG) | — | 262 | — | 250 | — | 1012 | — | |

EXAMPLE 2

Another embodiment of the process of this invention is set forth in Table II illustrated by a material balance, obtained in carrying out the process shown in FIG. 2. The block diagram of FIG. 2 represents the main process step. The material balance specifically applies to the process steps as numbered according to their conveying lines referring to FIG. 2.

The material balance computations are based on production of 100 pound moles per hour of a high heating value substitute natural gas from a shifted coal gasified effluent, corresponding in composition to that from Lurgi type gasifier. Operation of the process is similar to that described for Example 1 except that there are three primary methanation stages. The first, fourth, fifth and sixth stages employ the Union Oil type catalyst also used in Example 1 and the second and third stages employ a steam-hydrocarbon reforming catalyst also used in Example 1.

Table II summarizes the compositions and flow data for streams identified by the numerals of their conveying lines in FIG. 2 as follows:

TABLE II

| STREAM NO. | MATERIAL BALANCE PRODUCTION OF SNG | | | | | | | |
|---|---|---|---|---|---|---|---|---|
| | 328 | 340 | 355 | 365 | 371 | 375 | 381 | 383 |
| COMPONENT (M %) | | | | | | | | |
| INERTS | 1.6 | | 0.953 | 1.059 | 1.287 | 1.385 | 1.491 | 1.630 |
| $H_2$ | 61.7 | | 36.748 | 28.841 | 42.691 | 35.810 | 48.625 | 39.857 |
| $H_2O$ | | 100 | 40.441 | 45.349 | 26.235 | 30.432 | 15.370 | 20.414 |
| CO | 19.0 | | 11.316 | 1.875 | 9.093 | 4.369 | 11.611 | 7.019 |
| $CO_2$ | 1.0 | | 0.569 | 5.804 | 3.779 | 5.676 | 3.361 | 4.700 |
| $CH_4$ | 16.0 | | 9.529 | 17.072 | 16.620 | 22.328 | 19.196 | 26.380 |
| $C_2+$ | 0.7 | | 0.417 | 0.0 | 0.295 | 0.0 | 0.346 | 0.0 |
| FLOW RATE (LB. MOLES/HR.) | 68,470 | 10,380 | 25,670 | 23,100 | 39,930 | 37,010 | 73,460 | 67,220 |
| TEMPERATURE (° F) | — | — | 550 | 1200 | 900 | 1294 | 900 | 1359 |
| PRESSURE (PSIG) | — | — | — | 300 | — | 294 | — | 288 |
| STREAM NO. | 389 | 393 | 397 | 403 | 498 | 433 | 450 | |
| COMPONENT (M %) | | | | | | | | |
| INERTS | 1.630 | 1.848 | 1.848 | 2.009 | 3.331 | 3.628 | 3.986 | |
| $H_2$ | 39.857 | 24.695 | 24.695 | 11.115 | 18.430 | 2.481 | 2.726 | |

TABLE II-continued

| | | | | | | | |
|---|---|---|---|---|---|---|---|
| $H_2O$ | 20.414 | 30.262 | 30.262 | 39.912 | 0.365 | 9.086 | 0.093 |
| CO | 7.019 | 1.692 | 1.692 | 0.127 | 0.211 | 0.017 | 0.019 |
| $CO_2$ | 4.700 | 4.904 | 4.904 | 2.683 | 4.449 | 0.607 | 0.667 |
| $CH_4$ | 26.380 | 36.599 | 36.599 | 44.154 | 73.214 | 84.181 | 92.509 |
| FLOW RATE (LB. MOLES HR.) | 67,220 | 59,280 | 59,280 | 54,530 | 32,880 | 30,200 | 27,480 |
| TEMPERATURE (° F) | 550 | 1137 | 550 | 890 | 500 | 784 | 100 |
| PRESSURE (PSIG) | — | 268 | — | 256 | — | 1012 | — |

EXAMPLE 3

The coprecipitated nickel oxide-alumina catalyst of Example 1 containing about 47 weight percent of nickel oxide was tested in a piloe scale adiabatic reactor. The pilot plant unit simulated conditions which would occur in the primary reactors of commercial scale methanation units using a process of the type shown in FIG. 1 herein. This process omits the use of the conventional shift reactor and effects the methanation and water gas shift conversion steps simultaneously. The catalyst was subjected to the most severe conditions of the process, i.e., those of the first primary reactor wherein a feed stream of fresh reactant gas and steam is catalytically methanated.

One end of a 0.93 inch I.D. 0.020 inch wall tube was threaded into the bottom flange of and vertically aligned up the center of an 8 inch nominal schedule 80 cylindrical vertically oriented pressure vessel made of 316 stainless steel. The catalyst, composed of crushed ¼ inch pellets (secrrened to simulate ⅛ inch extrudate), was packed within the 0.93 inch I.D. 0.02 inch wall tube to form a catalyst bed having a depth of 36 inches. The void space between the catalyst bed tube and the inside walls of the pressure vessel was packed with high temperature Kaowool ceramic fiber insulation to minimize heat loss. (Kaowood blanket was obtained from the Babcock & Wilcox Company, Refractories Division, Old Savannah Road, Augusta, Georgia 30903). the pressure vessel to match the temperature zones in the catalyst and assure essentially adiabatic operation. The top of the catalyst bed (0.02 inch wall tube) was press fitted into the top flange adaptor. This allowed the insulation space to pressurize and permitted the use of thin wall tube to hold the catalyst bed since it saw no pressure differential. This minimized axial heat flow, and facilitated bed temperature measurements. Ten thermocouple probes were provided at intervals along the catalyst bed to indicate an accurate temperature profile within the catalyst bed.

The feed stream reacted comprised steam and a reactant gas. A separate vaporizer coil was used to generate high pressure steam (390 psig). The table below summarizes spot readings of reaction conditions during a 64 hour run. The feed stream was gradually lowered in temperature from about 700° F. to about 550° F. without loss in performance of the catalyst. Also the moles steam to moles reactant gas in the stream was adjusted from about 2 to about 1.2 without carbon deposition or loss in catalyst performance. Dry gas feed rate to the reactor was 15,000 VHSV (corresponding to a gas consumption of 5,000 SCFD).

Results of Gas Chromatography analysis of reaction conditions during the run are summarized in Table III below:

TABLE III

| Sample | Time on Stream, hrs. | Feed Temp, °F | Outlet °F | Steam (M) Gas (M) | Pressure (PSIG) | CO (M %) | $CH_4$(M %) | $CO_2$(M %) | $H_2$(M %) | $N_2$(M %) |
|---|---|---|---|---|---|---|---|---|---|---|
| Feed | 5 | — | — | — | — | 29.27 | 17.47 | — | 52.33 | .93 |
| Product | 5.4 | 716 | 1161 | 1.53 | 378 | 3.82 | 26.70 | 18.40 | 50.08 | 1.00 |
| Product | 9.5 | 651 | 1125 | 1.54 | 360 | 3.53 | 28.05 | 18.42 | 49.0 | 1.00 |
| Product | 13.3 | 599 | 1144 | 1.48 | 376 | 3.20 | 29.14 | 18.30 | 48.35 | 1.01 |
| Product | 17.0 | 601 | 1144 | 1.47 | 390 | 3.50 | 29.25 | 18.76 | 47.47 | 1.02 |
| Product | 20.3 | 601 | 1143 | 1.49 | 390 | 3.27 | 29.62 | 18.36 | 47.71 | 1.04 |
| Product | 30.7 | 608 | 1153 | 1.21 | 388 | 3.66 | 29.23 | 18.33 | 47.75 | 1.03 |
| Product | 36.8 | 601 | 1155 | 1.15 | 390 | 3.60 | 29.54 | 18.59 | 47.24 | 1.03 |
| Product | 44.3 | 556 | 1161 | 1.14 | 395 | 3.44 | 30.53 | 18.70 | 46.28 | 1.05 |
| Product | 56.9 | 545 | 1137 | 1.21 | 384 | 3.36 | 30.86 | 17.86 | 46.86 | 1.06 |
| Product | 64.9 | 549 | 1152 | 1.20 | 392 | 3.41 | 30.61 | 18.59 | 46.35 | 1.04 |

In the light of the foregoing disclosure, numerous alternate modes of practicing the present invention, but within its scope and spirit, will undoubtedly occur to persons familiar with the art. It is intended therefore that the specification and appended drawings be considered illustrative only and not construed in any limiting sense.

What is claimed is:

1. An improved process for the production of methane from hydrogen and carbon oxides comprising:
   (a) adiabatically reacting steam and a reactant gas comprising hydrogen and carbon oxides in an initial fixed bed, adiabatic, catalytic, primary reaction zone, said steam and reactant gas being employed at an inlet feed temperature above about the minimum initiation temperature of the catalyst in said zone, said catalyst being hydrothermally stable from said inlet temperature to a temperature between about 1100° F. and about 1200° F., said steam being employed in an amount sufficient to prevent both (1) carbon formation on the catalyst employed in mid process and (2) overheating of said catalyst, said reaction producing an effluent gas at an outlet temperature within said hydrothermal stability range of said catalyst;
   (b) adiabatically reacting said effluent gas and additional reactant gas comprising hydrogen and carbon oxides in an additional fixed bed, adiabatic, catalytic, primary reaction zone, said effluent gas and additional reactant gas being employed at an inlet temperature above about 900° F., said catalyst in the additional primary reaction zone comprising a steam-hydrocarbon reforming catalyst hydrothermally stable from said inlet feed temperature to a temperature between about 1250° F. and about 1600° F., said reaction producing further effluent gas at an outlet temperature of between about 1250° F. and about 1600° F.;

(c) cooling said further effluent gas from its outlet temperature to a secondary, wet, catalytic, reaction zone inlet temperature, said inlet temperature being above the minimum initiation temperature of the catalyst in said secondary zone;

(d) adiabatically reacting said cooled, further effluent gas in a secondary, wet, fixed bed, adiabatic, catalytic reaction zone, the catalyst in said secondary wet, catalytic reaction zone being essentially the same catalyst as employed in said initial primary reaction zone, thereby producing a product gas rich is methane, said product gas having a temperature below about the maximum operating temperature of said catalyst in said secondary reaction zone;

(e) condensing a substantial portion of the steam present in said product gas to water; and (f) removing said water from the product gas, whereby the exothermic methanation operation is carried out without the need for expensive internally cooled surfaces or high recycle rates, catalyst damage is minimized, carbon deposition during preheating is essentially eliminated and methane formation in the initial primary reaction zone is enhanced.

2. The process of claim 1 and including subjecting said product gas following water removal to at least one secondary, dry, fixed bed, adiabatic, catalytic reaction zone to convert residual $H_2$ and CO to methane and steam; and thereafter condensing a substantial portion of said steam in said product gas to water which is removed therefrom to provide a substitute natural gas.

3. The process of claim 2 wherein, the product gas subjected to said secondary dry reaction zones contains less than about 4 mole percent water.

4. A process as defined in claim 1 wherein in step a, the minimum initiation temperature of said first catalyst is between about 550° F. and about 700° F.

5. A process as defined in claim 4 wherein the minimum initiation temperature of said first catalyst is between about 550° F. and about 600° F.

6. A process as defined in claim 1 wherein the temperature of said reactant gas is between about 200° F. and about 500° F.

7. A process as defined in claim 6 wherein said reactant gas temperature is between about 250° F. and about 450° F.

8. A process as defined in claim 1 wherein the ratio of $H_2$ to CO in said reactant gas is between about 3–3.5 to 1.

9. A process as defined in claim 1 wherein there are three or four primary reaction zones.

10. A process as defined in claim 1 wherein said steam in step a is at a temperature between about 300° F. and about 800° F.

11. A process as defined in claim 1 wherein said first feed stream of step a is provided by first admixing said stem and said reactant gas and then heating said admixture to a temperature between about 550° F. and 700° F.

12. The process of claim 1 and including passing said further effluent gas from said additional primary reaction zone and additional reactant gas comprising hydrogen and carbon oxides to at least one further fixed bed, adiabatic, catalytic, primary reaction zone, said reactants having an inlet temperature above about 900° F. in each of said further primary reaction zones, said catalyst in each of said further primary reaction zones comprising a steam-hydrocarbon reforming catalyst hydrothermally stable from said inlet temperature to a temperature between about 1250° F. and about 1600° F., the effluent gas being produced in each of such further primary reaction zones being introduced into the next succeeding further primary reaction zone, the effluent gas from the last of said further primary reaction zones comprising said effluent gas subsequently cooled and reacted in said secondary wet reaction zone.

13. The process of claim 1 and including at least one additional secondary reaction zone, the product gas from the preceding secondary reaction zone comprising the feed gas for the next succeeding secondary reaction zone, the product gas from the last of said secondary reaction zones comprising said product gas from which said steam is condensed to water and removed therefrom.

14. The process of claim 12 and including at least one additional secondary reaction zone, the product gas from the preceding secondary reaction zone comprising the feed gas for the next succeeding secondary reaction zone, the product gas from the last of said secondary reaction zones comprising said product gas from which said steam is condensed to water and removed.

* * * * *